US007072502B2

(12) United States Patent
Hemar et al.

(10) Patent No.: US 7,072,502 B2
(45) Date of Patent: *Jul. 4, 2006

(54) ALTERNATING PHASE-SHIFT MASK INSPECTION METHOD AND APPARATUS

(75) Inventors: Shirley Hemar, Tel Aviv (IL); Alex Goldenshtein, Rishon Lexlon (IL); Gadi Greenberg, Tel-Aviv (IL); Mula Friedman, Nes Ziona (IL); Boaz Kenan, Rehovot (IL)

(73) Assignee: Applied Materials, Inc., Santa Clara, CA (US)

( * ) Notice: Subject to any disclaimer, the term of this patent is extended or adjusted under 35 U.S.C. 154(b) by 592 days.

This patent is subject to a terminal disclaimer.

(21) Appl. No.: 09/876,955

(22) Filed: Jun. 7, 2001

(65) Prior Publication Data

US 2002/0186879 A1    Dec. 12, 2002

(51) Int. Cl.
*G06K 9/00*    (2006.01)
(52) U.S. Cl. .................... 382/144; 382/149; 356/237.1
(58) Field of Classification Search ................ 382/144, 382/149; 356/237.1; 430/5, 30; 250/559, 250/45; 348/125, 126
See application file for complete search history.

(56) References Cited

U.S. PATENT DOCUMENTS

| 3,725,574 A | 4/1973 | Gast |
| 4,148,065 A | 4/1979 | Nakagawa et al. ......... 358/101 |
| 4,595,289 A | 6/1986 | Feldman et al. |
| 4,922,308 A | 5/1990 | Noguchi et al. ............ 356/237 |
| 4,926,489 A | 5/1990 | Danielson et al. |
| 5,114,223 A * | 5/1992 | Torigoe et al. ............. 353/101 |
| 5,210,635 A | 5/1993 | Nagata et al. |
| 5,272,116 A | 12/1993 | Hosono ....................... 437/228 |
| 5,441,834 A | 8/1995 | Takekuma et al. ............. 430/5 |
| 5,481,624 A | 1/1996 | Kamon ....................... 382/144 |
| 5,563,702 A | 10/1996 | Emery et al. |
| 5,572,598 A | 11/1996 | Wihl et al. .................. 382/144 |

(Continued)

FOREIGN PATENT DOCUMENTS

EP    0 628 806 A2    12/1994

OTHER PUBLICATIONS

"Improving Resolution in Photolithography with a Phase Shifting Mask" by Marc D. Levenson et al. in IEEE Transactions on Electron Devices, vol. ED-29, No. 12, Dec. 1982.

(Continued)

*Primary Examiner*—Bhavesh M. Mehta
*Assistant Examiner*—John B. Strege
(74) *Attorney, Agent, or Firm*—Sughrue Mion PLLC

(57) ABSTRACT

A reticle inspection system and method for complete and fast inspection of phase shift mask reticles, both for incoming inspection and for periodic and pre-exposure inspection tool, is employable by facilities such as mask shops as an inspection tool compatible to the mask shop's customers. The inventive system and method detect phase errors in an aerial image by acquiring the image of the phase shift mask under the same optical conditions as the exposure conditions (i.e. wavelength, numerical aperture, sigma, and illumination aperture type). Images are acquired at a positive out-of-focus and a negative out-of-focus, and are compared in order to enhance possible phase error. The term "phase error" refers to the acceptable range of the phase deviation from the programmed 180° on the phase shift mask, by using the exposure system to achieve the image on the photoresist, satisfying the requirements of the wafer specification.

33 Claims, 4 Drawing Sheets

U.S. PATENT DOCUMENTS

| | | | |
|---|---|---|---|
| 5,576,829 A | 11/1996 | Shiraishi et al. | |
| 5,744,381 A | 4/1998 | Tabata et al. | 438/16 |
| 5,745,168 A | 4/1998 | Ninomiya | 348/191 |
| 5,795,688 A | 8/1998 | Burdorf et al. | |
| 5,838,433 A | 11/1998 | Hagiwara | |
| 5,892,579 A | 4/1999 | Elyasaf et al. | |
| 5,965,306 A | 10/1999 | Mansfield et al. | |
| 6,016,357 A | 1/2000 | Neary et al. | 382/144 |
| 6,018,392 A | 1/2000 | Tzu et al. | 356/351 |
| 6,025,905 A | 2/2000 | Sussman | 356/3.01 |
| 6,052,478 A | 4/2000 | Wihl et al. | 382/144 |
| 6,072,898 A | 6/2000 | Beaty et al. | 382/146 |
| 6,075,883 A | 6/2000 | Stern et al. | 382/144 |
| 6,078,393 A * | 6/2000 | Oohashi et al. | 356/511 |
| 6,078,738 A | 6/2000 | Garza et al. | 395/500.22 |
| 6,081,659 A | 6/2000 | Garza et al. | 395/500.22 |
| 6,091,845 A | 7/2000 | Pierrat et al. | 382/144 |
| 6,124,924 A | 9/2000 | Feldman et al. | |
| 6,148,097 A | 11/2000 | Nakayama et al. | 382/141 |
| 6,268,093 B1 * | 7/2001 | Kenan et al. | 430/30 |
| 6,327,033 B1 * | 12/2001 | Ferguson et al. | 356/394 |
| 6,335,129 B1 | 1/2002 | Asano et al. | |
| 6,466,315 B1 | 10/2002 | Karpol et al. | |
| 6,580,502 B1 * | 6/2003 | Kuwabara | 356/237.3 |
| 2002/0171825 A1 | 11/2002 | Krantz et al. | |

OTHER PUBLICATIONS

Budd et al., "A New Mask Evaluation Tool, The Microlithography Simulation Microscope Aerial Image Measurement System," *Optical / Laser Microlithography 7*, San Jose, Mar. 2-4, 1994, Proceedings of SPIE, Optical/Laser Microlithography, Bellingham, SPIE, US vol. 2197, pp. 530-540.

Martino et al., "Application of the Aerial Image Measurement System (AIMS) to the Analysis of Binary Mask Imaging and Resolution Enhancement Techniques," *Optical / Laser Microlithography 7*, San Jose, Mar. 2-4, 1994, Proceedings of SPIE, Optical/Laser Microlithography, Bellingham, SPIE, US vol. 2197, pp. 573-584.

Ferguson, Richard A., et al., "Application of an Aerial Image Measurement System to Mask Fabrication and Analysis," *SPIE vol. 2087 13th Annual Symposium on Photomask Technology and Management*, Sep. 22-23, 1993, Santa Clara, California, pp. 131-144.

Budd, Russell A., et al., "A New Tool for Phase Shift Mask Evaluation, the Stepper Equivalent Aerial Image Measurement System—AIMS™," *SPIE* vol. 2087 Photomask Technology and Management (1993).

Schenker, Richard, "Comparison of Single and Dual Exposure Phase Shift Mask Approaches for Poly Gate Patterning," *SPIE*, vol. 3546, Sep. 1998.

\* cited by examiner

ALTERNATING PHASE-SHIFT MASK INSPECTION METHOD AND APPARATUS

BACKGROUND OF THE INVENTION

1. Field of the Invention

This invention relates to techniques for inspecting reticles that are used in fabricating microelectronic devices through a microphotolithographic process. Particularly, the present invention relates to a method and an apparatus for detecting defects by emulating the operation of a specific photolithography tool in which a reticle is to be used. Such a tool may be an optical exposure system including optical steppers, scanners, and step-and-scan exposure systems. The invention is embodied in a method and an apparatus that can be used readily for inspecting reticles in the industrial environment.

More particularly, the present invention relates to a method and apparatus for inspecting phase shift masks used in a microphotolithographic process. A phase shift mask (PSM) uses destructive interference to control intensity of coherent light exposing a wafer during a manufacturing process. Closely spaced apertures are constructed in such a way that any light passing through any particular aperture will be 180 degrees out of phase with respect to light passing through adjacent apertures. As a result, any light that spills into the dark region between adjacent apertures will cancel out or destructively interfere. At the middle of the particular aperture, the light from the adjacent aperture is constructively interfering. The destructive interference reduces unwanted exposure in the center of the dark region and allows smaller features to be etched on wafers. This effect occurs also when the image is not focused, so that image degradation because of focus error is significantly reduced. In lithographic terms, it extends the depth of focus (DOF). The physics of PSM is described by M. D. Levinson, N. S. Viswanathan, and R. A. Simpson in *Improving resolution in photolithography with a PSM*, an IEEE publication, vol. ED-29, No. 12, December 1982.

The combined effect of the focus error and phase error can be simplified by the following description, graphically shown in FIG. 4. Focus error contributes to a global phase error $\delta\phi$, and mask phase errors introduce $\Delta\phi$ to a programmed 180° phase region. At a region of constructive interference, the intensity is a result of an amplitude sum of a particular feature plus an adjacent feature with phase and focus contribution: $A(180°+\Delta\phi)+A(0°+180°+\delta\phi)$. The phase mask error $\delta\phi$ will be positive for positive defocus, and assuming that the global phase error $\delta\phi$ approximates the mask phase error $\Delta\phi$, the interference will be between corresponding phases (most constructive result). For the best focus the phase difference will be $\Delta\phi$(a less constructive interference). For negative defocus, the phase difference will be $2\cdot\Delta\phi$ (the lowest amount of interference). The comparison of the positive defocus image to the negative one will give a much larger difference signal than a comparison of images taken with normal focus.

Regions that phase shift light may be created by etching or deposition techniques. According to one technique, the mask substrate may be etched to a precise depth such that the light passing through that region is phase shifted by 180 degrees. Phase altering materials also may be deposited on a substrate.

2. Description of the Related Art

Modern microelectronic devices are commonly produced using a photolithographic process. In this process, a semiconductor wafer is first coated with a layer of photoresist. This photoresist layer is then exposed to illuminating light using a photomask (for simplicity, the terms photomask, mask, and reticle will be used here interchangeably) and subsequently developed. After the development, non-exposed photoresist is removed, and the exposed photoresist produces the image of the mask on the wafer. Thereafter, the uppermost layer of the wafer is etched. Thereafter, the remaining photoresist is stripped. For multilayer wafers, the above procedure is then repeated to produce subsequent patterned layers.

Increasing the number of components in microelectronic circuits produced using the above photolithographic process requires the use of very high resolution images in photoresist exposure. The major limitations on the resolution of the image that can be projected on the photoresist are created by the illuminating light diffraction effects on the features of the mask and the limitations on the quality of the mask itself. The diffraction effects become important when the wavelength of the electromagnetic radiation used in the exposure of the photoresist becomes significant with respect to the size of the features of the mask being reproduced during the exposure. Increasing the resolution and decreasing the size of the reproducible features of the projected images may be achieved by decreasing the wavelength of the light that is being used in the photoresist exposure. For this reason, it is advantageous to use the electromagnetic radiation in the ultraviolet region of the spectrum, which corresponds to the shorter wavelength. In particular, ultraviolet i-line (365 nm), deep UV (248 nm), 193 nm, and 157 nm wavelengths have been used. Extreme Ultraviolet (11–13 nm) wavelengths are known; it is expected to be within contemplation that such wavelengths may be used as well.

Another method for increasing the resolution of the image is the use of RET (Resolution Enhancement Techniques) which include: off axis illumination, OPC (Optical Proximity Correction) reticles, and PSM (Phase Shift Mask) reticles.

It should be appreciated by those skilled in the art that to produce an operational microelectronic circuit, a mask must be as defect-free as possible, and preferably should be completely defect-free. Therefore, mask inspection tools are needed to detect various defects in the masks that can potentially reduce microelectronic circuit fabrication yields. Smaller feature sizes of the masks used in the microphotolithographic process, as well as the use of the phase shift masks and OPC masks, require more sophisticated tools for mask inspection. For instance, the inspection of phase shift masks requires not only finding "conventional" defects, such as particles, but also detecting errors in the thickness of various regions of the mask. Numerous systems for mask inspection have been developed in response to the growing demands of the electronic industry.

Early mask inspection tools used actual photoresist exposure to study the quality of the mask. According to this method, the mask is placed on the optical exposure system and used to actually expose the photoresist. The image obtained in this way then is studied to determine whether the mask performs to specifications. Because this method is expensive, time-consuming, and often inaccurate, it is uneconomical and inefficient.

Certain kinds of mask defects (called "surface" defects, for example, a particle on the surface of a mask) can be detected by inspecting the mask using the image of the mask produced by the light transmitted through the mask and the light reflected by one face of the mask. The mask inspection tool that uses this method acquires both images and analyzes them. The results of the analysis of the two images yield the information on the condition of the mask. Other systems use die-to-die comparison, die-to-database comparison, or reflected image to transmitted image comparison. In the die-to-die comparison method, the acquired images of a die of the mask are compared to the images of another die from the same mask. In the die-to-database method, the acquired images are compared to images that are simulated using the design specifications.

Such an inspection system can detect defects that may or may not print on the photoresist during the actual photolithographic process. The major drawback of this method is that it studies the physical structure of the mask independently of the optical image actually produced by the mask on the wafer. For instance, variations in the line width of the image that the mask produces frequently are higher than the corresponding variation in the line width of the mask itself. This phenomenon is called MEEF (Mask Error Enhancement Factor). Another example is PSM, in which there is no visible relation between phase error and the printed image. Therefore, it is desirable to relate the physical structure of the mask to the actual image that the mask creates on the photoresist, and to study directly the image that the mask actually produces.

In order to facilitate the evaluation of the mask performance during the mask development stage, IBM Corporation has developed a microscope called the Aerial Image Measurement System (AIMS™) that uses an aerial imaging method for mask evaluation. The Zeiss MSM100, a mask development tool, implementing AIMS™ technology, is available commercially from Carl Zeiss, GmbH of Germany. The MSM100 system can be used to evaluate the printability properties of newly developed masks.

An aerial imaging method is described in European Patent Application No. 0628806. According to this method, the inspection system simulates an optical exposure system that is used to expose the photoresist during semiconductor device fabrication. The optical system of the mask inspection device uses a set of the exposure conditions, used in the actual microphotolithographic process, to create an image that would be produced on the photoresist during actual device fabrication. In particular, the system matches the wavelength, the partial coherence of the exposure light, illumination aperture and the imaging numerical aperture NA of the optical exposure system. The created aerial image is magnified and detected using a CCD camera that is sensitive to ultraviolet radiation.

In addition to evaluation of the mask design, the use of the aerial imaging method permits the detection of the mask defects that would print during the actual microphotolithographic process. Almost any kind of defect on the reticle, including a particle on the transparent region, a pin-hole, a pin-dot, an edge truncation, etc., causes line width variation in the printed image. The term "line width" used herein describes a set of parameters of the image produced by the reticle on the photoresist, such as wire-to-wire distances, that determine whether the reticle is to be rejected as defective. The acquired aerial images are analyzed using the AIMS™ software, also developed by IBM. Despite all the above advantages, the Zeiss/IBM system has limited application as a printability review station for a set of detected defects by other inspection systems.

U.S. Pat. No. 5,481,624 describes a system that uses aerial imaging for die-to-database inspection of phase shift masks. According to the described inspection method, an aerial image produced by a phase-shift mask is verified against the original circuit pattern that was used in manufacturing the mask.

U.S. Pat. No. 5,795,688 discloses a system that uses an aerial imaging method for inspection of microphotolithographic masks having optical proximity corrections using a die-to-database comparison. In this system, an aerial image of a mask manufactured using the aforementioned optical proximity corrections is compared to an aerial image of the same mask obtained by simulation. Various defects in the mask, such as missing chrome, contamination, glass damage, phase defects, and transmission errors are identified as discrepancies between the two images. The simulation process takes into account optical proximity effects due to the limited resolution of the optical exposure system and the proximity effects due to the photoresist etching during the mask manufacturing process. The simulated aerial image can be obtained using the original mask design or, alternatively, using the mask design corrected for optical proximity effects.

Despite the above advances in the mask inspection technology, at the present time there is no inspection tool that would fulfill the demands of the industry. The IBM system is designed for mask development labs, and not for production stage mask inspection, and therefore does not possess adequate automation.

Also, the inspection methods based on die-to-database comparison that are used by the existing aerial imaging systems are not always effective, especially for highly complicated mask designs. The die-to-database comparison method uses models describing the behavior of an optical exposure system, as well as the effects of the etching used in the mask manufacturing process to produce the simulated image used in the mask inspection. However, the actual mask is different from the mask design because of limitations of the mask writing tool. As a result, there are limitations in the accuracy of the transformation from database to aerial image. Inadequate simulation can lead to a significant number of "nuisance" defects—the discrepancies between the acquired aerial image and the simulated image being caused not by the presence of actual defects in the mask, but by inadequacies in the simulation model. Nuisance defects can greatly complicate the mask inspection. For all the foregoing reasons, the limitations on the quality of the simulated images limit the performance of the aerial imaging inspection techniques that use the die-to-database comparison.

Accordingly, there is a need for a mask inspection system that would make it possible to detect errors in the line width of the image that the mask would actually produce on the photoresist.

The system also must be capable of detecting the phase defects and the presence of surface defects such as particles, contaminations, coating defects, and the like.

It also is desirable for the mask inspection system to provide speedy and reliable identification of the above mask defects. Such a system would be able to work efficiently in a clean manufacturing environment such as fabs and mask shops and increase the productivity thereof.

SUMMARY OF THE INVENTION

In view of the foregoing, it is one feature of the present invention to provide an inspection system that provides more complete information on the properties of the photolithographic mask. Particularly, it is a feature of the present invention to provide a mask inspection system capable of detecting phase errors using unfocused images.

It is yet another feature of the present invention to provide a mask inspection system that provides speedy and reliable identification of the above mask defects.

To implement the above features and achieve the advantages of the present invention, there is provided a method for inspecting a multiple die reticle that is used with an optical exposure system under a set of exposure conditions, the multiple die reticle including at least a first and a second die. In accordance with the inventive method, a plurality of images of the reticle is acquired using transmitted light under the indicated exposure conditions. The plurality of images of the reticle includes images of the first die and images of the second die. Each of the plurality of images of the reticle corresponds to a different focal condition. The images of the first die and the second die are used to detect variations in line width in the first die.

Also in accordance with the invention, an apparatus is provided which can be used to practice the inventive method. In one embodiment, the apparatus includes a scanner for acquiring a plurality of images of the multiple die reticle under the set of exposure conditions. The plurality of images includes images of the first die and images of the second die. The apparatus also includes an image processing module for detecting variations in line width of the first die by comparing the images of the first die and the images of the second die.

In accordance with yet another aspect of the invention, the just-described scanner unit is used in a manner more specific to phase shift masks, to take advantage of defect characteristics in phase shift masks. According to a still further aspect of the invention, a simplified apparatus for phase shift mask inspection (single and multiple die masks) is provided.

Also in accordance with the invention, an apparatus is provided including: a laser light source; a homogenizer and a transmission light illumination means for illuminating the reticle; and an optical system for producing a plurality of magnified images of the reticle under the set of exposure conditions, the optical system having variable illuminating and imaging apertures for reproducing the indicated set of exposure conditions. The plurality of acquired images of the reticle includes images of the first die and images of the second die. The inventive apparatus also includes an image acquisition module for acquiring the plurality of magnified images of the reticle; and an image processing module for analyzing a condition of the reticle by comparing the images of the first die and the images of the second die. The apparatus also may include an optical system for acquiring dark field reflection images, though for purposes of accomplishing the inventive method, the dark field portions of the system are not necessary. As a result, apparatus such as that disclosed in copending, commonly assigned U.S. application Ser. No. 09/417,518, filed Oct. 13, 1999, the disclosure of which is incorporated by reference herein, may be used.

The above-mentioned and other attendant advantages of the present invention will become more apparent upon examination of the following detailed description of the embodiments thereof with reference to the attached drawing figures.

DETAILED DESCRIPTION OF THE PREFERRED EMBODIMENTS

The system for defect detection according to the present invention is composed of three main modules: (1) a scanner module; (2) a defect detection image processing hardware module; and (3) a post process and review station. The scanner module scans the reticle and acquires aerial images of the reticle in transmitted light at a plurality of focal planes, preferably three in one embodiment, and also may acquire dark field images of the reticle in reflected light at one focal plane. As will be seen, for phase shift masks, dark field imaging may be omitted. Additionally, serial images in two focal planes, rather than three, may be obtained, to take advantage of defect identification in phase shift masks based on the information that out of focus images provide.

By properly adjusting the apertures of the illuminating and imaging parts of the optical system, the NA and the coherence factor are adjusted. The optical system of the scanner module simulates the behavior of an optical exposure system and, as a result, the acquired transmission light aerial images are optically equivalent to those produced on the photoresist under a given set of exposure conditions. The image processing module then uses the acquired images to detect the defects in the reticle.

A software-based post process and review station reviews and analyzes the images of the detected defects through the focus range of the exposure system.

There now follows a detailed description of the three modules of the inventive reticle inspection apparatus and their methods of operation.

Scanner Unit

Preferably, the scanner unit scans the entire active area of the reticle and acquires sequentially three aerial images at different focal planes. The scanner unit supplies the scanned images of the detected defects acquired during scanning for off-line review. The scanner unit is also capable of acquiring additional aerial images of the detected defects at additional focal planes during the review stage.

Figure 1:
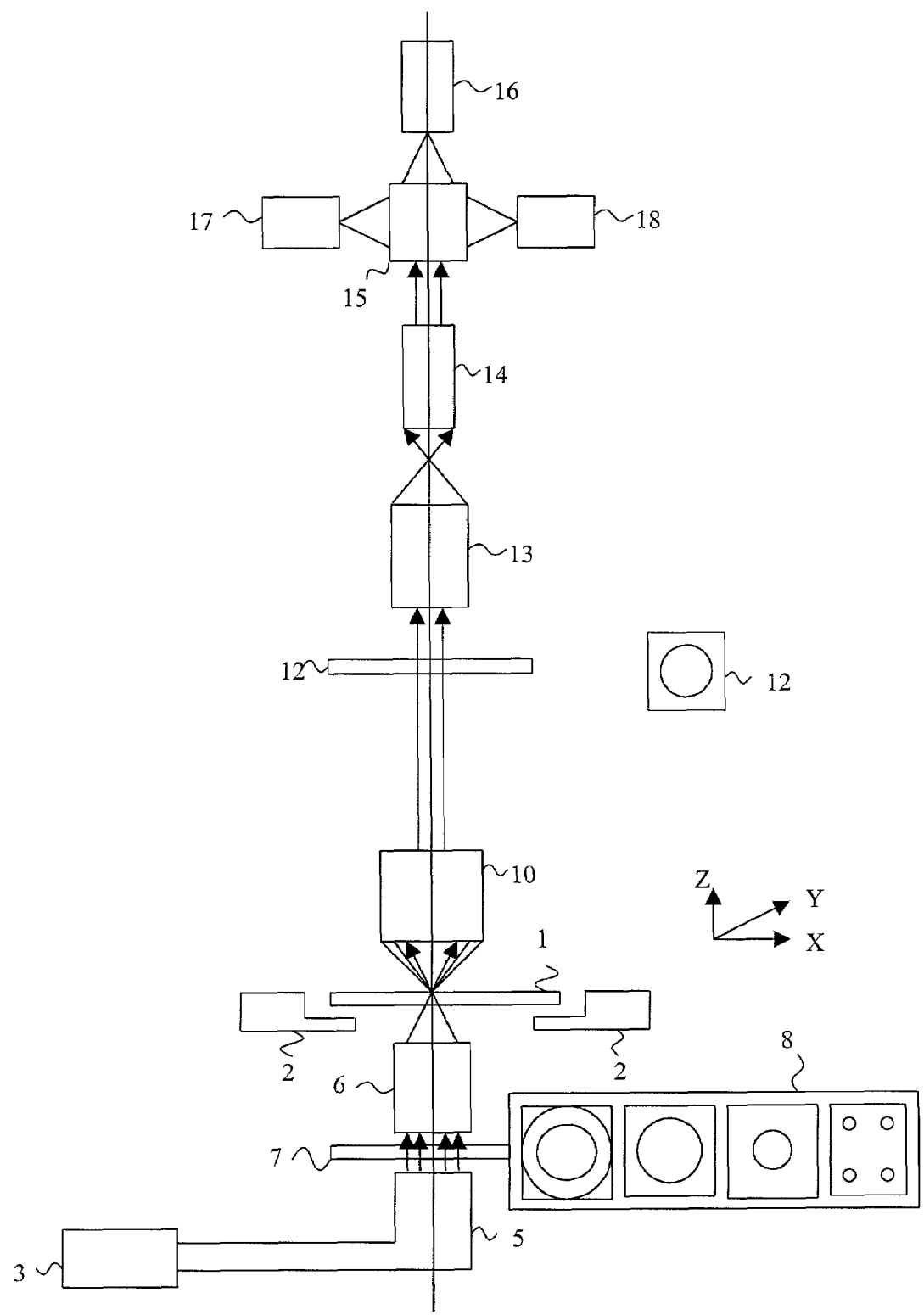
FIG. 1 is a schematic diagram of a scanner unit of the reticle inspection system according to an embodiment of the present invention.

FIG. 1 illustrates the internal organization of the scanner unit. The scanner unit includes many of the components of an optical microscope column. With reference to FIG. 1, the scanner scans a reticle 1 fixed on a moving stage 2. While the stage 2 is shown as movable, the stage could be fixed, and the scanner movable. As a yet further alternative, both the stage 2 and the scanner could be movable. It is relative movement between the scanner and the reticle that is important. Laser light from a light source 3 is used to illuminate the reticle 1. The light source 3 preferably is a pulsed laser source, but the light source 3 could also operate continuously. The radiation provided by the light source 3 preferably has the exact wavelength of the exposure system, with which the reticle is designed to be exposed, for example deep UV (248 nm), 193 nm, 157 nm, or EUV (11–13 nm).

When the scanner module acquires the aerial images of the reticle, the bottom surface of the reticle is illuminated using a transmission light illumination system which includes a homogenizer and illumination optics 5, an illumination aperture 7, and a condenser 6. The homogenizer has a function, among others, of reducing speckle resulting from the use of a coherent illumination source. The structure of the homogenizer is not critical, so long as the homogenizer reduces speckle appropriately. The aerial images of the reticle 1 acquired by the scanner module simulate the images that would be produced by the reticle 1 on the photoresist, when the reticle 1 is placed on an optical exposure system. In this mode, the radiation from the illuminating light source 3 passes through the homogenizer and illumination optics 5 and the condenser 6. The condenser 6 reduces the diameter of the illuminating beam of light in the reticle plane to just a little more than the size of the field of view of the imaging system. Between the condenser 6 and the homogenizer and illumination optics 5 there is an illumination numerical aperture 7 ($NA_{ill}$), the size and the shape of which can be changed by an illumination aperture changer 8. Adjusting the size and the shape of the illumination aperture 7 permits reproduction of the illumination and the coherence conditions of the photoresist exposure tool. In particular, the aperture 7 is selected to set the proper coherence ratio sigma and to choose between on axis and off axis illumination such as a quadruple or an annular mode of illumination, as described below.

The objective 10 collects the light transmitted by the reticle 1 in the transmission light illumination operating mode. As shown in the above-mentioned copending application, the objective 10 also can collect the light reflected by the reticle in the dark field illumination operating mode. After passing through the objective 10, the light passes through the collecting adjustable numerical aperture diaphragm 12, which is situated in the optically designed aperture stop surface or a conjugate surface. The size of the collecting numerical aperture diaphragm 12 is selected to reproduce the operating conditions of the exposure system used in the microphotolithographic process. Therefore, the aerial image of the reticle 1 created by the optical system of the reticle inspection apparatus according to the invention is equivalent to the image produced on the photoresist by the optical exposure system during the microphotolithographic process.

The light emerging from the numerical aperture 12 is then focused by a lens, such as tube lens 13 to produce an image of the reticle 1. This image is then magnified by a zoom magnification lens 14. After passing through the zoom magnification lens 14, the light beam is being split by a beam splitter 15 to produce three images of the reticle in the three CCD cameras of the reticle inspection apparatus: a first focus camera 16, a second focus camera 17, and a third focus camera 18. It should be noted that while the use of three CCD cameras presently is preferred in one embodiment, the invention is not limited to this number of CCD cameras. Any camera configuration or combination that produces the desired three images of the reticle may be used. As will be seen below, in dealing with phase shift masks in particular, two defocus images, rather than three images, may be used.

In another embodiment of the invention the system is equipped with a suitable auto-focusing system (not specifically shown) aimed at maintaining the inspection plane of the reticle in the focal plane of the objective 10. This is generally done by providing motion of the stage 2, or the objective 10, or both, in the Z direction.

The reticle 1 is illuminated by the transmission light illumination system 5 and the three images of the reticle in the transmitted light are simultaneously acquired by the first focus camera 16, the second focus camera 17, and the third focus camera 18. During this operating mode, the first focus camera 16 is in focus, while the second and the third focus cameras 17 and 18 are defocused. The second focus camera 17 is at positive defocus, while the third focus camera 18 is at negative defocus. It should be noted that the aerial images of the reticle created in the cameras 16-18 are significantly magnified (typically ×50–×200). For this reason, the distance between marginal allowed focal planes is so magnified, as to allow a large variation in the positions of the focal planes of the cameras. The positions of these focal planes can be adjusted by conventional mechanical means.

The method of operation of the inventive reticle inspection apparatus is described below. In one embodiment, the stage 2 moves the reticle 1 in such a way that the scanner unit scans the reticle, slice-by-slice, in a serpentine manner. Again, relative movement between the stage 2 and the scanner unit may be in any known manner which enables the scanning. Also, serpentine scanning is not critical to the invention, so long as the scanning is complete. The width of a slice preferably is the width of the optical field of view of the system. The CCD cameras 16, 17, and 18 can be line CCD devices capable of simultaneously acquiring an image of the entire slice of the reticle 1. Alternatively, CCD cameras 16, 17, and 18 can be of a shift-delay type. Preferably, the cameras 16–18 are sensitive in the ultraviolet range, particularly in the deep UV range. Sensitivity in the extreme UV range also is contemplated.

In one embodiment of the invention, the moving stage 2 and the reticle 1 move in a continuous manner. The CCD cameras 16, 17, and 18 are triggered by the stage 2 to acquire the image of the slice of the reticle 1 every time the stage has passed one field of view. Preferably, the image of the reticle is acquired by shooting a laser pulse from laser source 3 through the illumination optics 5 of the system and acquiring the images with digital area cameras 16–18 through the imaging optics. It will be appreciated that if the pulsed laser source is used to illuminate the reticle, the reticle need not be stationary at the time of the image capture and, for this reason, the reticle can be moved continuously. The same result can be achieved through using a short exposure time for the cameras 16–18. In another embodiment of the invention, the stage 2 and the reticle 1 move in a stepwise manner. In yet another embodiment, the stage 2 and reticle 1 may be stationary, and the light moved to scan the reticle in a desired manner. Relative movement between the stage 2 and the scanner may be employed to achieve the desired scanning.

As can be appreciated, when the apertures 7 and 12 are inserted into the beam's path during the transmission light illumination mode, the optics of the scanner unit emulates the optics of an exposure tool. Particularly, the illumination aperture 7 selectively alters the effective illuminating $NA_{ill}$ of the condenser 6, while the aperture 12 changes the collection numerical aperture $NA_{coll}$ of the objective 10. A ratio of the $NA_{ill}$ to the $NA_{coll}$ is called a pupil filling ratio of the objective and is responsible for the coherence of the reticle illumination. The smaller the value of the pupil filling ratio, the higher the coherence of the reticle illumination. Note that the numerical aperture 7 can have more complex configuration, for example four small apertures displaced with respect to the axis of the beam. Other illumination aperture configurations can be used to emulate different exposure systems and their interaction with the reticle.

In addition to determining the coherence of the illuminating light, the illumination numerical aperture 7 can be used to shape the light beam to more closely resemble the exposure tool. To that end, the illumination aperture 7 may be a diffractive optical element or a proper apodization aperture affecting also the shape of the incident beam. The aperture 7 can provide a flat-top beam, i.e. a beam with uniform intensity distribution over the cross-section of the beam. Accordingly, by adjusting the shape and the size of the numerical apertures 7 and 12, the inspection tool emulates the illuminating conditions of the exposure tool, including its effective NA, the coherence of the illumination, and the shape of the illuminating beam. For every field of view, three images are acquired at different focal planes. By properly adjusting the size of the numerical apertures 7 and 12, the system simulates the behavior of an optical exposure system and, as the result, the acquired aerial images are optically equivalent to those produced on the photoresist under a given set of exposure conditions.

The different focus images of the reticle 1 are acquired with three CCD cameras 16–18 at different focal conditions. Preferably, the digital data from each camera is compensated for distortion, registration error, illumination non-uniformity, and the camera's pixel non-uniformity. The corrected data is sent with the synchronization signal to the image processing module. A main controller computer (not shown) controls the scanner.

In yet another embodiment particularly useful for detecting defects in phase shift masks, the images captured by the second and third focus cameras 17 and 18 are compared with each other. Because the light passing through the phase shift regions is modified, only the image created by transmitted light is representative of the image displayed on the wafer. An image taken at one defocus plane shows phase defects brighter than the background, while an image taken at the other defocus plane shows phase defects darker than the background. By comparing the images taken at the two defocus planes, any phase defects are revealed in double contrast to the background. No comparison with another die or database is required to detect such phase defects.

Preferably, the scanner unit also includes a hardware synchronization module (not shown) which synchronizes the system, and creates dummy signals for diagnostics purposes. The movement of the stage 2 is monitored by a laser interferometer (not shown) that generates a clock for the system. The synchronization module uses this clock to synchronize the laser pulses from the illuminating laser source 3 and the exposures of the cameras 16–18. The compensation cards (not shown) compensate for optical image distortions, registration errors, variations of the camera pixels' sensitivity, and variations of the laser pulses' intensity. The conditions of the scan are set by the operator through the main control computer (not shown) to match the exposure conditions (NA, sigma, aperture type) and the detection sensitivity (magnification).

Figure 2:
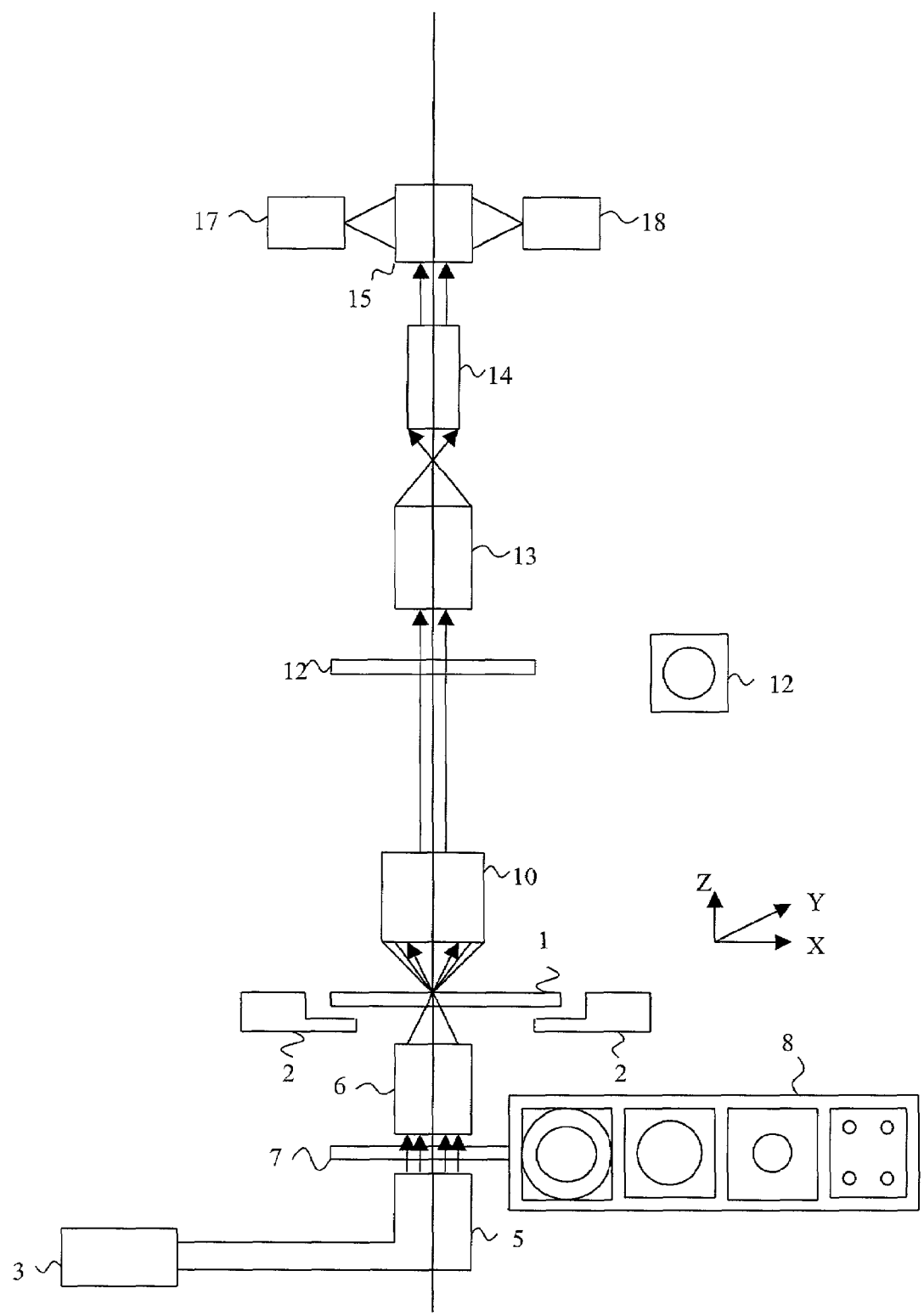
FIG. 2 is a schematic diagram of a scanner unit for inspecting phase shift masks according to another embodiment of the present invention.

This embodiment may be practiced by the apparatus described in FIG. 1, however the first, in-focus CCD camera 16 is not necessary. FIG. 2 shows the apparatus of FIG. 1, but without the first focus camera. As noted previously, the apparatus shown in the above-mentioned copending application, having not only the three cameras but also dark field imaging apparatus, in which one of the cameras is involved in the dark-field imaging, may be employed to practice the inventive apparatus.

The scanner transmits digital images, synchronization and clock signals to the image processing module. The image data transmission lines can be made sufficiently long to permit the scanner unit and the image processing module to be in different locations. Preferably, the scanner can be used by the post process and review station through the main computer to grab images of the defects at various focus positions.

Image Processing Module

Preferably, the image-processing module is a real-time image-processor that finds defects in the imaged pattern generated using the scanner unit. The streams of image data will comprise in focus and two different kinds of out of focus image data in one embodiment. In another embodiment, two different out of focus streams can be compared with each other to identify defects in phase shift masks.

While the reticle is scanned slice after slice, the information about the existence of phase defects or phase variations is recorded according to the mask coordinates. Phase variation is a quantitative value, which can be used to evaluate the actual phase error using a post process option. The above recorded information is used to create a defect or phase variation map.

Post Process and Review Station

The post process and review station is used to automatically analyze the image data. It also enables the user to review the suspected defects detected with the image processing module. Preferably, the post process and review station is software-based and operates on a computer workstation. Reticle defects detected using die-to-die comparison of aerial images can be studied further, and classified by comparing the acquired aerial images to the simulated aerial images, which can be obtained using simulation software. For example, one of the widely available simulation software packages (AIMS™, VSS™, Sigma C, Finley™) can be adapted for this purpose. The AIMS™ software was designed by IBM Corporation to be used on the MSM100 tool and can simulate the aerial images of the phase shift masks, as well as the masks having optical proximity corrections. The VSS™ and Finley™ software packages can run on a general purpose computer. These packages input the exposure conditions, such as the exposure system's NA, and produce the simulated image by emulating the behavior of the reticles as well as that of the photoresist. This simulated image is used to conduct additional, more accurate study and classification of the detected defects.

Preferably, the post process and review station is operated using a user-friendly graphical user interface. The post process and review station has several modes of operation.

The post process and review station reviews and classifies the detected defects at the user control. According to an embodiment of the invention, the user can select a defect from the defect list created by the image processing module. In response, the system displays the detected defects and the corresponding good die aerial images at the focal points of the scan on the monitor screen. In this embodiment, the line width measurements of the defective and good features (at the wafer plane) can be calculated according to the user's request. The system is also capable of performing a calculation on the probability of the defect printability. According to this embodiment, images at a larger number of focal points are grabbed at the user's request and processed immediately by a more accurate overlapping process window.

In another embodiment, more accurate analysis is accomplished using on-line review of the defects. In this embodiment, high NA, high-resolution images of the defects, are acquired. This enables one to visualize the actual defects on the reticle, especially those defects that cause the line width variations on the wafer.

In another embodiment of the invention, the system uses the results of the phase error evaluation for individual dies of the reticle 1 to generate a map of the phase variations for the entire reticle. The generated map is then displayed to the user in a graphical format. For instance, different areas of the reticle having different values of the phase variations may be drawn in different colors. Such a map provides a very useful method for visualizing how the amount of variation in phase changes from die-to-die on the reticle. For example, it is important to see how the amount of variation in phase is different for the peripheral dies, as compared to the central dies.

Figure 3:
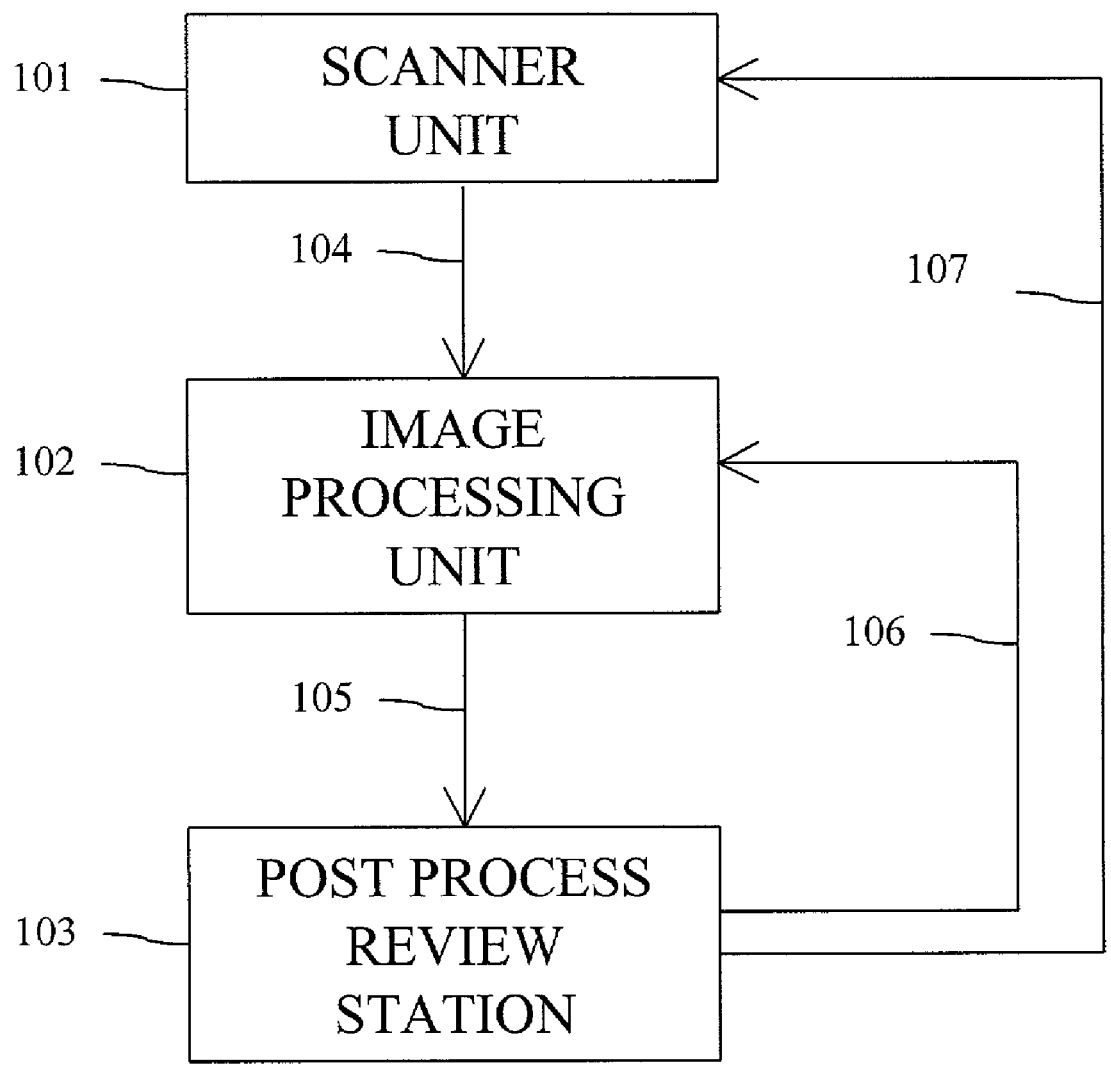
FIG. 3 is a block diagram of the reticle inspection system according to an embodiment of the present invention.
Figure 4:
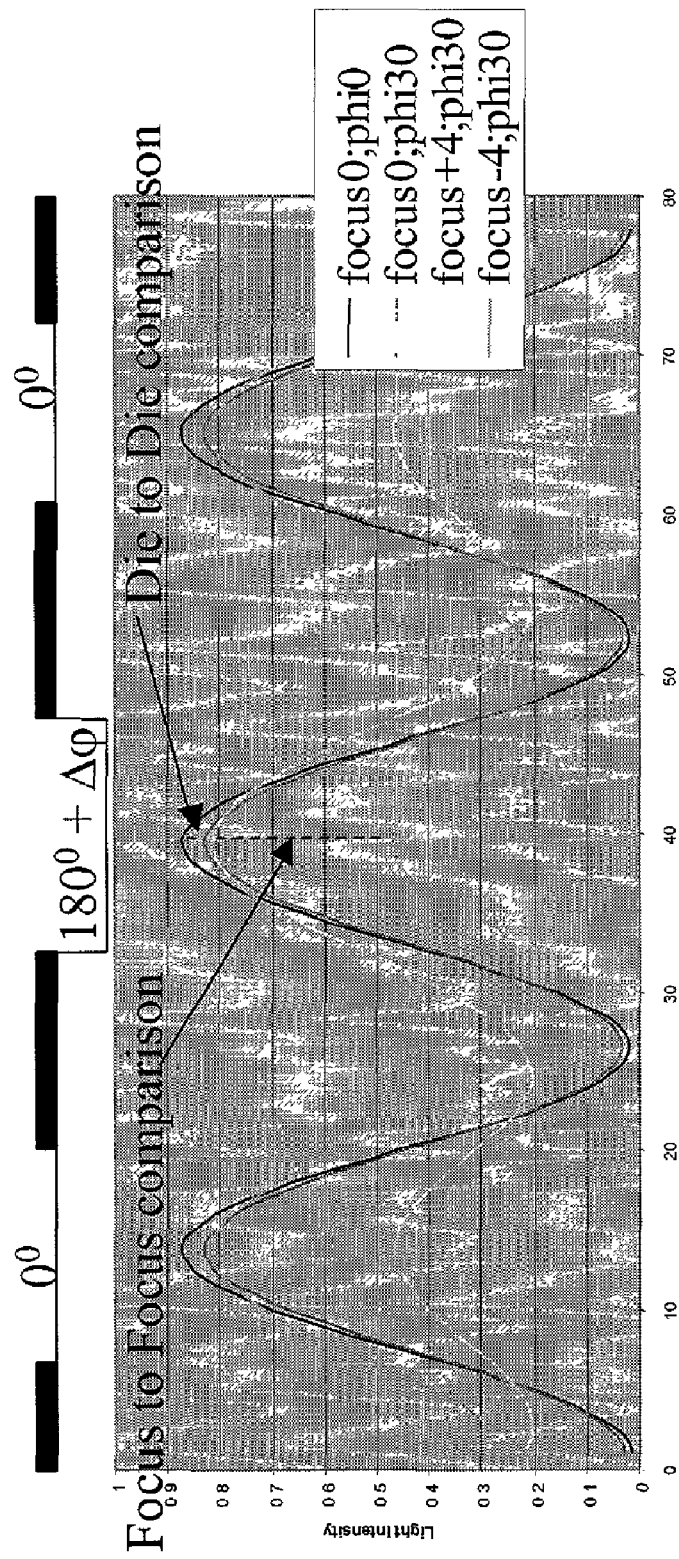
FIG. 4 illustrates physical phenomena of phase error impact, which is used in another embodiment of the present invention.

FIG. 3 shows a block diagram illustrating the operation of the reticle inspection system according to an embodiment of the invention. With reference to FIG. 3, the scanner unit 101 acquires images of the reticle and transmits the image data 104 to the image processing unit 102 for processing. The image processing unit 102 performs processing of the image data and detects defects in the reticle. After that, the image processing unit 102 transmits the processed image data 105 of the defective and good dies to the post process and review station 103 for subsequent analysis and display. The post process and review station can send control signals 106 and 107 to the image processing unit and the scanner unit. If additional images are needed in the process of image analysis in the post process and review station, such as images from additional focus surfaces, the post process and review sends request 107 to the scanner unit 101 to grab additional images and request 106 to the image processing unit to process those additional images.

While the invention has been described herein using preferred embodiments thereof, it will be readily appreciated by those skilled in the art that various modifications in form and detail may be made therein without departing from the scope and spirit of the invention.

What is claimed is:

1. A method for inspecting a phase shift mask that is used with a photolithographic optical exposure system under a set of exposure conditions, said method comprising:
   acquiring a plurality of aerial images produced by said phase shift mask using a transmitted light, said plurality of aerial images being acquired in an aerial imaging inspection system and within a process window of said exposure system by emulating said set of exposure conditions; said plurality of aerial images including a first and a second aerial image produced by said phase shift mask; wherein said first aerial image produced by said phase shift mask is in a first out of focus condition, and said second aerial image produced by said phase shift mask is in a second out of focus condition; and
   comparing said first and said second aerial images to each other to detect phase defects and errors in said phase shift mask, wherein
   said first and said second aerial images are concurrently produced from the same light transmitted by the mask; and,
   wherein prior to said comparison step, said first and second aerial images are transformed to simulate a behavior of an exposure system and photoresist.

2. The method of claim 1, wherein said first out of focus condition is a positive out of focus condition, and said second out of focus condition is a negative out of focus condition.

3. The method of claim 1, wherein said acquired aerial images produced by said phase shift mask are magnified in relation to corresponding images created on photoresist by said optical exposure system using said phase shift mask.

4. The method of claim 1, further comprising automatically processing results of said comparison.

5. The method of claim 1, further comprising using results of said comparison to produce a map of said variations in said phase of said phase shift mask for the entire phase shift mask.

6. The method of claim 1, wherein said transmitted light is provided using a pulsating light source.

7. The method of claim 6, wherein said pulsating light source is a pulsating laser.

8. The method of claim 1, wherein said acquiring said plurality of aerial images comprises providing continuous relative movement between said transmitted light and said phase shift mask.

9. The method of claim 6, wherein said acquiring said plurality of aerial images comprises providing continuous relative movement between said laser and said phase shift mask.

10. An apparatus for inspecting a phase shift mask that is used with an optical exposure system under a set of exposure conditions, said apparatus comprising:
    a scanner for acquiring a plurality of aerial images produced by light transmitted through said phase shift mask while emulating said set of exposure conditions; said plurality of aerial images generated by said phase shift mask comprising a first and a second aerial image generated by said phase shift mask; wherein said first aerial image generated by said phase shift mask is in a first out of focus condition, and said second aerial image generated by said phase shift mask is in a second out of focus condition; and
    an image processing module for detecting variations in phase of said phase shift mask by, first transforming said first and second aerial images to simulate a behavior of an exposure system and photoresist and then comparing said first and said second aerial images generated by said phase shift mask to each other, wherein
    said first and said second aerial images are concurrently produced from the same light transmitted by the mask.

11. The apparatus according to claim 10, wherein said first out of focus condition is a positive out of focus condition, and said second out of focus condition is a negative out of focus condition.

12. The apparatus according to claim 10, wherein said scanner comprises a plurality of cameras for acquiring said plurality of aerial images generated by said phase shift mask.

13. The apparatus according to claim 12, wherein said plurality of cameras comprises:
    a first camera for acquiring said first image generated by said phase shift mask; and
    a second camera for acquiring said second image generated by said phase shift mask.

14. The apparatus according to claim 13, wherein:
    said first camera is out of focus in a positive direction; and
    said second camera is out of focus in a negative direction.

15. The apparatus according to claim 12, wherein:
    said scanner further comprises a light source for illuminating said phase shift mask with an illuminating light; and
    said plurality of cameras are sensitive to said illuminating light.

16. The apparatus according to claim 15, wherein said light source is a pulsating light source.

17. The apparatus according to claim 16, wherein said pulsating light source is a pulsating laser.

18. The apparatus according to claim 10, further comprising a means for effecting continuous relative movement between said scanner and said phase shift mask.

19. The apparatus according to claim 16, further comprising a means for effecting continuous relative movement between said laser and said phase shift mask.

20. The apparatus according to claim 13, wherein said scanner further comprises:
   a transmission light illumination system for illuminating said phase shift mask; and
   an optical system for collecting light emerging from said phase shift mask and creating aerial images generated by said phase shift mask in said first and said second cameras.

21. The apparatus according to claim 20, wherein said optical system of said scanner further comprises a numerical aperture diaphragm for reproducing said set of exposure conditions.

22. An apparatus for inspecting a phase shift mask that is used with an optical exposure system under a set of exposure conditions, said apparatus comprising:
   a light source;
   transmission light illumination means for illuminating said phase shift mask;
   optical means for producing a plurality of magnified aerial images generated by said phase shift mask while emulating said set of exposure conditions, said optical means having a numerical aperture diaphragm for reproducing said set of exposure conditions;
   imaging means for acquiring said plurality of magnified aerial images generated by said phase shift mask; said plurality of aerial images generated by said phase shift mask comprising a first and a second aerial images generated by said phase shift mask; wherein said first aerial image generated by said phase shift mask is in a first out of focus condition, and said second aerial image generated by said phase shift mask is in a second out of focus condition; and
   image processing means for analyzing a condition of said phase shift mask using said plurality of aerial images generated by said phase shift mask, wherein said first and said second aerial images generated by said phase shift mask are first transformed to simulate the behavior of an exposure system and a photoresist and then compared to each other and said first and said second aerial images are concurrently produced from the same light transmitted by the mask.

23. The apparatus according to claim 22, wherein said first out of focus condition is a positive out of focus condition, and said second out of focus condition is a negative our of focus condition.

24. The apparatus according to claim 22, wherein said light source is a pulsating light source.

25. The apparatus according to claim 24, wherein said pulsating light source is a pulsating laser.

26. The apparatus according to claim 22, further comprising a means for effecting continuous relative movement between said scanner and said phase shift mask.

27. The apparatus according to claim 25, further comprising a means for effecting continuous relative movement between said laser and said phase shift mask.

28. The apparatus according to claim 22, wherein said imaging means further comprises a plurality of cameras for acquiring said plurality of magnified aerial images generated by said phase shift mask when the phase shift mask is illuminated by said transmission light illumination means.

29. The apparatus according to claim 28, wherein said plurality of cameras comprises:
   a first camera for acquiring said first image generated by said phase shift mask;
   a second camera for acquiring said second image generated by said phase shift mask; and
   said first and said second aerial images generated by said phase shift mask being respectively acquired by said first and said second cameras when the phase shift mask is illuminated by said transmission light illumination means.

30. The apparatus according to claim 29, wherein:
   said first camera is out of focus in a positive direction; and
   said second camera is out of focus in a negative direction.

31. The apparatus according to claim 22, further comprising a post process and review means for displaying said condition of said phase shift mask in a graphical form.

32. The apparatus according to claim 29, wherein:
   a wavelength of the light source is identical to the wavelength of the exposure system; and
   said first and said second cameras are sensitive to said spectrum of said light source.

33. The apparatus according to claim 22 further comprising a homogenizer disposed in the vicinity of said transmission light illumination means for reducing speckle resulting from use of said light source.

* * * * *